United States Patent [19]
Lee

[11] Patent Number: 5,957,134
[45] Date of Patent: Sep. 28, 1999

[54] ANESTHESIA DELIVERY SYSTEM

[76] Inventor: Han Shik Lee, 134 The Dell, Searingtown, N.Y. 11507

[21] Appl. No.: 08/979,655

[22] Filed: Nov. 18, 1997

[51] Int. Cl.$^6$ .................................................. A61M 16/00
[52] U.S. Cl. ................................ 128/207.14; 128/207.15
[58] Field of Search .......................... 128/200.26, 207.14, 128/207.15, 207.29

[56] References Cited

U.S. PATENT DOCUMENTS

| | | | |
|---|---|---|---|
| 3,815,606 | 6/1974 | Mazal | 128/207.16 |
| 4,022,219 | 5/1977 | Basta | 128/207.14 |
| 4,246,897 | 1/1981 | Muto | 128/207.29 |
| 4,256,099 | 3/1981 | Dryden | 128/207.15 |
| 4,595,005 | 6/1986 | Jinotti | 128/207.14 |
| 4,850,371 | 7/1989 | Broadhurst et al. | 128/207.14 |
| 5,291,882 | 3/1994 | Makhoul et al. | 128/207.14 |
| 5,544,648 | 8/1996 | Fischer, Jr. | 128/207.14 |
| 5,546,930 | 8/1996 | Wikefeldt | 128/207.14 |
| 5,669,380 | 9/1997 | Garry et al. | 128/207.14 |
| 5,687,714 | 11/1997 | Kolobow et al. | 128/207.14 |
| 5,765,558 | 6/1998 | Psaros et al. | 128/207.14 |
| 5,823,184 | 10/1998 | Gross | 128/207.14 |

*Primary Examiner*—Aaron J. Lewis
*Attorney, Agent, or Firm*—Allen R. Morganstern, Esq.

[57] ABSTRACT

This invention relates to a new and improved anesthesia delivery system utilized in medical procedures wherein there is minimized build up of carbon dioxide levels in a patient due to a patient re-breathing their own exhaled gases. The anesthesia delivery system comprises a first tubular element hermetically coupled to a source of gas which is inhaled by a patient, and a second tubular element hermetically coupled to a system for expelling gas exhaled from a patient's lungs such that when a patient is intubated with the delivery system, the end of the first tubular element is positioned adjacent the patient's pharynx while the end of the second tubular element is positioned within the patient's trachea. For that portion of the delivery system that is positioned within the mouth and pharynx of a patient, the first tubular element is adjacent the wall of the second tubular element while the portion of the first and second tubular element structure that is outside the body of a patient has the first tubular element concentrically positioned within the second tubular element. An inflatable balloon is provided about the exterior of the second tubular element that is positioned within the trachea of a patient when the system is utilized which is capable of being selectively inflated or deflated. Furthermore, a separate hollow tubular structure capable of selectively removing gas from within the second tubular element has one of its ends positioned at a point where the first tubular element is coupled to the second tubular element.

8 Claims, 3 Drawing Sheets

ANESTHESIA DELIVERY SYSTEM

BACKGROUND AND OBJECTS OF THE INVENTION

This invention relates to a new and improved delivery system to be utilized during a medical procedure where anesthesia is required, the delivery system minimizing by its utilization the build up of carbon dioxide levels that a patient may be exposed to due to a patient re-breathing their own exhaled gases. The delivery system comprises a first tubular element hermetically coupled to a source of gas which is inhaled by a patient, and a second tubular element hermetically coupled to a system for the disposing of gas expelled from a patient's lungs such that when a patient is intubated upon utilization of the delivery system, the end of the first tubular element of the system is positioned adjacent to the patient's pharynx and the end of the second tubular element of the system is positioned in the patient's trachea. For that portion of the delivery system that is positioned within the mouth and pharynx of a patient, the first tubular element is adjacent to the wall of the second tubular element while the portion of the first and second tubular element structure that is outside the body of a patient has the first tubular element concentrically positioned within the second tubular element. Additionally, there is provided an inflatable balloon about the exterior of the lower tubular element of the system that is positioned within the trachea of a patient when the system is utilized which is capable of being selectively inflated or deflated. Furthermore, there is also provided a separate tubular structure capable of selectively removing gas from within the second tubular element of the system at a point where the first tubular element is coupled to the second tubular element.

It is well recognized that in any anesthetic delivery system there is the necessity to minimize what has been termed "dead space", which means that volume within the system that allows for the re-inhaling back into the lungs of a patient of an exhaled volume of gas and its inherent carbon dioxide content. Since excessive carbon dioxide levels can cause extreme medical consequences to a patient undergoing a surgical procedure, inherent in any anesthetic system is the necessity to minimize within the system the build up of carbon dioxide levels.

Although there exists in the prior art systems for the delivery of anesthesia which address the concerns associated with the build up of carbon dioxide levels in a patient, the prior art devices and the methodology addressed therein do not address themselves to the instant invention and its unique design and advantages which, in part, address the carbon dioxide "dead space" concerns.

In conjunction with the prior art that addresses itself to anesthetic and related delivery systems, it should be noted that the following patents neither teach nor disclose the patentable features and/or patentable design of the present invention.

More particularly, the prior art referred to above is as follows: U.S. Pat. No. 5,309,906, entitled "Endobronchial Tube Assembly", issued to LaBombard on May 10, 1994; U.S. Pat. No. 5,372,131, entitled "Triangular Intratracheal Tube", issued to Heinen on Dec. 13, 1994; U.S. Pat. No. 4,233,984, entitled "Respiratory Ventilating Device", issued to Walling on Nov. 18, 1980; and U.S. Pat. No. 4,265,235, entitled "Anesthetic System", issued to Fukunaga on May 5, 1981.

In keeping with the invention, it is a specific object of the invention to create a new and improved anesthetic delivery system wherein the "dead space" inherent in the design of an anesthetic delivery system and which occurs in the utilization thereof is reduced to a minimum to thus minimize the re-introduction into a patient's lungs of expelled carbon dioxide gas.

It is another object of the invention to create a new and improved anesthetic delivery system wherein, inherent in the design of said system there is achieved the ability to have the incoming gas warmed by the gas being expelled from the system.

It is another object of the invention to create a new and improved anesthetic delivery system wherein, inherent in the design of said system there is achieved the ability to extend the length of the breathing circuit without creating additional "dead space".

It is another object of the invention to create a new and improved anesthetic delivery system wherein, inherent in the design of said system there is achieved the ability to utilize a balloon device that can be selectively inflated and/or deflated so as to prevent leaking of a gas past the point of the inflated balloon.

It is another object of the invention to create a new and improved anesthetic delivery system wherein, inherent in the design of said system, there is achieved the ability to utilize a separate tubular structure capable of selectively removing gas from the system on a selective basis so as to readily analyze same and thus monitor the carbon dioxide levels, as well as the oxygen levels and other anesthetic gas levels as related to a patient.

It is another object of the invention to create a new and improved anesthetic delivery system wherein the design of the system does not create a visual obstruction to a doctor during intubation.

It is another object of the invention to create a new and improved anesthetic delivery system wherein the design of the system does not impede the passage of gas out of the patient's lungs.

It is another object of the invention to create a new and improved anesthetic delivery system wherein there is utilized a filter capable of maintaining the moisture level within a patient's pulmonary tree while blocking the expelling of contaminants without incurring any "dead space".

The objects and advantages of the invention are set forth in part herein and in part will be obvious herefrom, or may be learned by practice of the invention, the same being realized and attained by means of the instrumentalities and combinations pointed out in the appended claims.

The invention consists in the novel parts, constructions, arrangements, combinations and improvements herein shown and described.

DESCRIPTION OF PREFERRED EMBODIMENT

Figure 1:
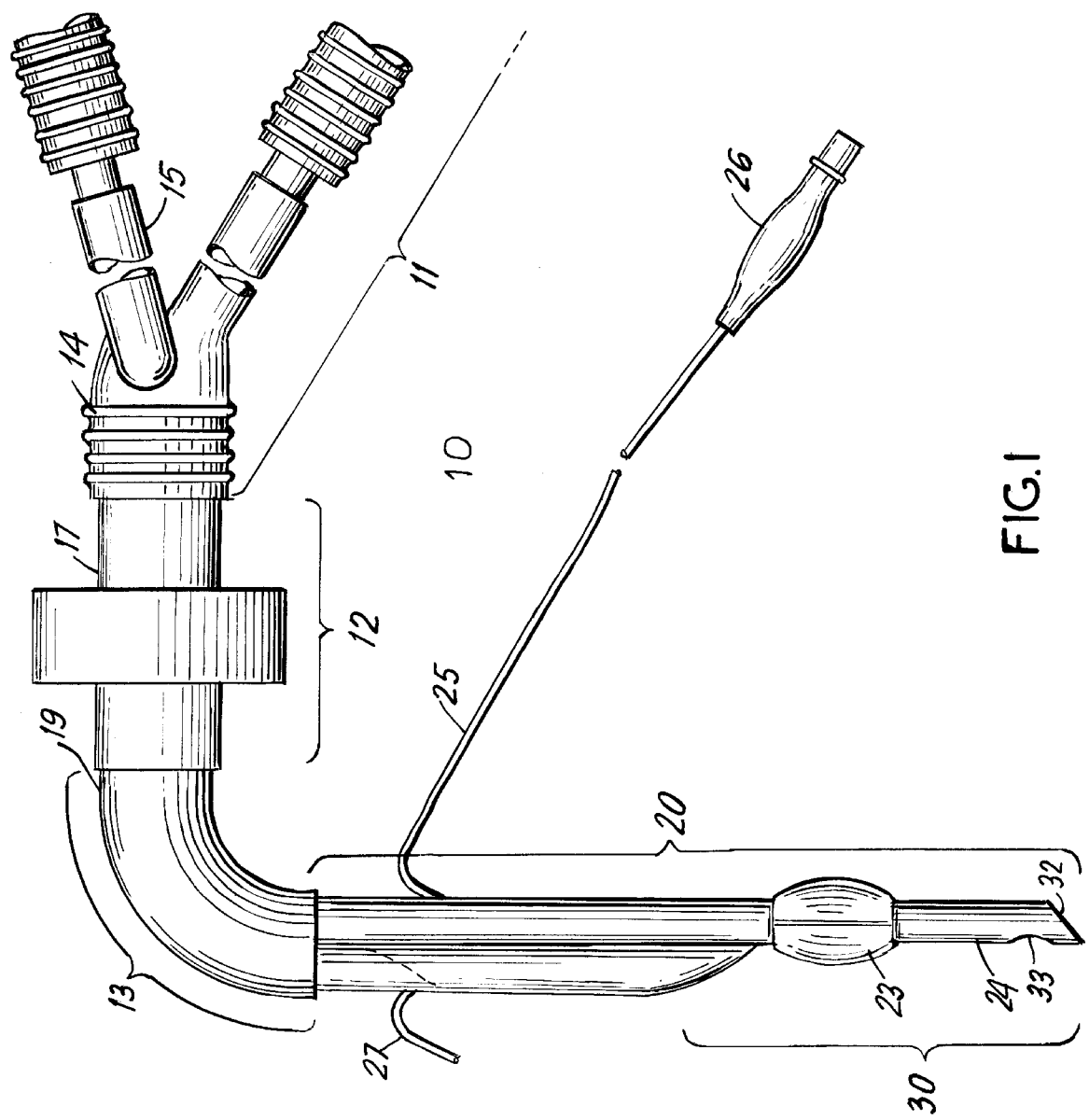
FIG. 1 is a front elevational view of a new and improved anesthetic delivery system evidencing the present invention.

Reference is herein made to FIG. 1 wherein there is illustrated a front elevational view of the new and improved anesthetic delivery system 10 constructed in accordance with the invention.

More particularly, it should be noted that anesthetic delivery system 10 as illustrated in FIG. 1, addresses itself to various components, which, when assembled, form the system, and thereby accomplish the overall goals and features of the invention.

Figure 2:
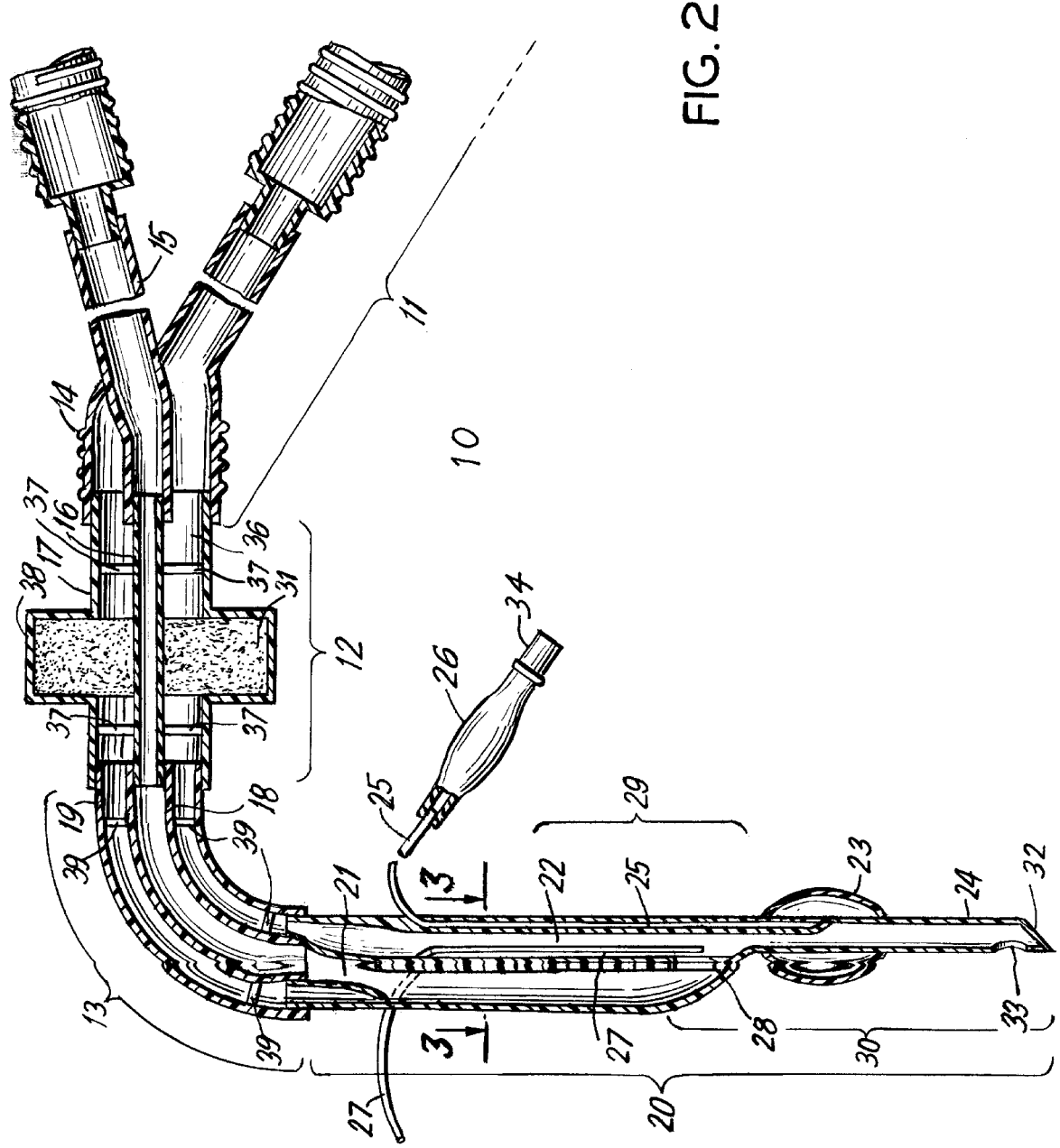
FIG. 2 is a cross-sectional view of the anesthetic delivery system depicted in FIG. 1 taken along its entire length.

As illustrated in FIG. 1, anesthetic delivery system 10 comprises coupling element 11, filter element 12, elbow element 13, and endo-tracheal tube element 20. It should be noted that coupling element 11, filter element 12 and elbow element 13, as depicted in FIG. 1, illustrate a preferred embodiment of anesthetic delivery system 10. Nothing herein should be considered as limiting the scope of the invention to the particular structures as illustrated in FIGS. 1 and 2 for coupling element 11, filter element 12, and elbow element 13 since equivalents thereto can be addressed without detracting from the invention. As will be more fully set forth hereinafter, as long as a means exist for providing an hermetically sealed path to endo-tracheal tubular element 20 for the introduction into a patient of an exterior source of gas whose composition can be selectively mixed for purposes of delivering anesthesia as well as a separate and distinct hermetically sealed path for disposing of expelled gas from a patient's lungs, one is able to carry out and otherwise practice the invention. It should further be noted that the invention is not limited to the utilization of coupling element 11, and/or filter element 12, and/or elbow element 13 in combination with endo-tracheal tube element 20, but rather, the invention can be practiced with or without coupling element 11, and/or filtering element 12, and/or elbow element 13 in combination with endo-tracheal tube element 20, there only being required means to supply to and expel from endo-tracheal tubular element 20 gases as herein set forth by the utilization of structural components that define two separate and distinct gaseous passageways coupled to endo-tracheal tubular element 20 in accordance with the invention.

In keeping with the invention and as further illustrated in FIG. 2, which is a cross-sectional view of anesthetic delivery system 10 as depicted in FIG. 1, two separate and distinct gaseous passageways are established upon the assemblage of coupling element 11, filter element 12, elbow element 13, and endo-tracheal tubular element 20, such that a gaseous composition can be delivered to the tracheal area of a patient once anesthetic delivery system 10 is in place.

Figure 4:
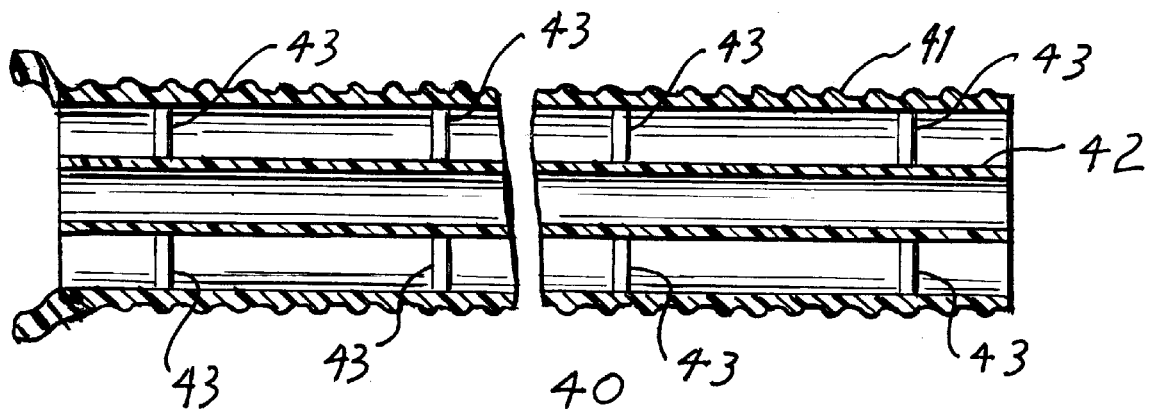
FIG. 4 is a cross-sectional view of extension element 40 which is capable of being inserted between coupling element 11 and filter element 12.

More particularly, and as illustrated in FIG. 2, coupling element 11 comprises outer tubular element 14 and inner tubular element 15. As illustrated therein and in keeping with the invention, outer tubular element 14 is coupled to an exterior element (not shown) capable of receiving expelled gas from a patient and disposing of it in a manner well known in the prior art. Inner tubular element 15 is coupled to an exterior source of gas (not shown) whose composition can be selectively mixed and regulated in a manner well known in the prior art. Although, outer tubular element 14 and inner tubular element 15 as illustrated in FIG. 2 do not evidence any particular length, it is within the scope of the invention for the lengths to vary from that of a foot or so in length to a length measuring upwards of tens of feet, the latter allowing for anesthetic delivery system 10 to be utilized by patients who are required to be placed in diagnostic devices such as an MRI or who will undergo various procedures that require the delivery to the patient of anesthesia from a remote source. Additionally, and as illustrated in FIG. 4, and as will be more fully set forth hereinafter, it is within the scope of the invention to utilize extension element 40 by insertion thereof between coupling element 11 and filtering element 12 as a further means to allow for the utilization of anesthetic delivery system 10 in circumstances wherein a patient is placed in diagnostic devises such as an MRI or when a patient will undergo various procedures that require the delivery to a patient of anesthesia from remote sources.

As further illustrated in FIG. 2, although filter element 12 utilizes prior art filtering materials to achieve the filtering of contaminants from the expelled gases as well as the preventing of moisture loss through the expelled gases, same however are utilized within a new, unique and novel structure as herein set forth whereby filter element 12 does not result in the addition of any "dead space" to anesthesia delivery system 10 by its utilization. More particularly, filter element 12 comprises an outer tubular element 17 defining a hollow cylindrical chamber 36 which has passing therethrough in axial alignment inner tubular element 16, inner tubular element 16 being structurally centered within outer tubular element 17 by spatially positioned spoke members 37. It should be noted that nothing should be considered to limit the invention to the fact that inner tubular element 16 is structurally positioned in axial alignment with outer tubular element 17 by utilization of spoke members 37, since any well-known prior art means to so position inner tubular element 16 in axial alignment with outer tubular element 17 is within the scope of this invention.

As illustrated in FIG. 2, inner tubular element 15 of coupling element 11 is of a diameter sufficient to be selectively hermetically coupled to inner tubular element 16 of filter element 12 while outer tubular element 17 of filter element 12 is of a diameter so as to be capable of being selectively hermetically coupled to outer tubular element 14 of coupling element 11. As illustrated in FIG. 2, inner tubular element 16 provides a hermetically sealed path through the center of outer tubular element 17 of filter element 12 for the passage of an exterior source of gas whose composition can be selectively mixed so as to deliver anesthesia to a patient. As a result of the fact that inner tubular element 16 provides a hermetically sealed pathway through the center of outer tubular element 17 of filter element 12, there is created a structure whereby carbon dioxide expelled by a patient and passing through outer tubular element 17 of filter element 12 cannot be introduced back into a patient's lungs by introduction into inner tubular element 16 of filter element 12. As a result, the unique structure of filter element 12 as depicted in FIG. 2 prevents any further "dead space" being introduced into anesthetic delivery system 10 by the utilization of filter element 12.

In keeping with the invention, outer tubular element 17 of filter element 12 further defines a cylindrical chamber 38 axially aligned with chamber 36 and contiguous therewith the diameter of chamber 38 being greater than the diameter of chamber 36.

As further illustrated in FIG. 2, filtering material 31 is placed within cylindrical chamber 38 of filter element 12 and can consist of any one of a number of well-known prior art compositions capable of achieving the desired filtering and moisture controls, to wit, compositions of fiberglass, foam and/or paper.

As further illustrated in FIG. 2, elbow element 13 comprises two concentric tubular elements, inner tubular element 18 and outer tubular element 19, inner tubular element 18 being structurally centered within outer tubular element 19 by spatially positioned spoke members 39. It should be noted that nothing should be considered to limit the invention to the fact that inner tubular element 18 is structurally positioned in axial alignment with outer tubular element 19 by utilization of spoke members 39, since any well-known prior art means to so position inner tubular element 18 in axial alignment with outer tubular element 19 is within the scope of this invention. It should be further noted that inner tubular element 18 of elbow element 13 is of a diameter capable of being selectively hermetically coupled to inner tubular element 16 of filter element 12. Similarly, outer tubular element 19 of elbow element 13 is of a diameter capable of being selectively hermetically coupled to outer tubular element 17 of filter element 12.

As a result, and consistent with the invention, there is the ability to selectively assemble and/or break down into components the various elements of anesthetic delivery system 10, to wit, coupling element 11, filtering element 12, elbow element 13 and endo-tracheal tubular element 20.

As a further feature inherent in the design of aesthetic delivery system 10, as associated with filter element 12 and elbow element 13, the incoming gaseous mixture carried through inner tubular element 15, inner tubular element 16, and inner tubular element 18 is heated by the expelled gases from a patient as a result of passing through the center of outer tubular element 17 and outer tubular element 19.

As further illustrated in FIG. 2, endo-tracheal tubular element 20 is the component of anesthetic delivery system 10 which is inserted through the mouth of a patient and past the patient's vocal cords such that its furthest end point, as evidenced by end portion 32 when endo-tracheal tubular element 20 is in place, is positioned within the patient's trachea.

As illustrated in FIG. 2, endo-tracheal tubular element 20 comprises a first tubular element 21 and a second tubular element 22. As illustrated in FIG. 2, first tubular element 21 is of a diameter at one end thereof so as to be selectively hermetically coupled to inner tubular element 18 of elbow element 13. Similarly, second tubular element 22 is of a diameter at one end thereof so as to be selectively hermetically coupled to outer tubular element 19 of elbow element 13.

Figure 3:
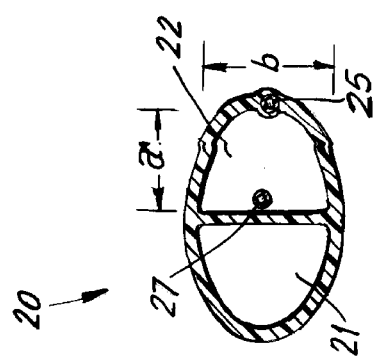
FIG. 3 is a cross-sectional view taken along lines 3—3 of FIG. 2.

It should be noted that whereas first tubular element 21 is initially concentrically centered within second tubular element 22 at the point where first tubular element 21 and second tubular element 22 are selectively hermetically coupled to elbow element 13 as referred to above, first tubular element 21 and second tubular element 22 become adjacent to each other as illustrated in FIG. 2 and as illustrated in FIG. 3, FIG. 3 being a cross-sectional view taken along lines 3—3 of FIG. 2. As a result, the portion of endo-tracheal tubular element 20 that is inserted through the mouth and down to the trachea of a patient, no longer defines a circular cross section comparable to the diameter of endo-tracheal tubular element 20 where same hermetically couples with elbow element 13, but rather, there is created, as illustrated in FIG. 3, an oval-like structure which inherently, by such a shape, facilitates the insertion of endo-tracheal tubular element 20 through the patient's mouth and past a patient's vocal cords and down to the patient's trachea.

As further illustrated in FIG. 2, endo-tracheal tubular element 20 additionally comprises inflatable balloon member 23 positioned about the exterior wall of lower tubular element 24 such that, upon the selective inflation of inflatable balloon element 23 when anesthetic delivery system 10 is in place, there is created an airtight seal between a patient's trachea and the exterior of endo-tracheal tubular element 20 such that only gases can flow through the interior of lower tubular element 24, first tubular element 21 and second tubular element 22 of endo-tracheal tubular element 20, as related to gases passing into and out of a patient's lungs. It should be noted that lower tubular element 24 is a component part of endo-tracheal tubular element 20 whose interior directly couples with the interior of second tubular element 22 where first tubular element 21 couples with the interior of second tubular element 22 as indicated by opening 28. In the preferred embodiment illustrated in FIG. 2, endo-tracheal tubular element 20 is 30 centimeters in length, however, nothing should be interpreted to so limit the invention, it being within the scope of the invention for the overall length of endo-tracheal tubular element 20 to be either greater or lesser than 30 centimeters depending upon the size of the intended patient.

As additionally illustrated in FIG. 2, lower tubular element 24 comprises the lower portion of endo-tracheal tubular element 20 and is positioned within a patient so that end portion 32 of lower tubular element 24 rests within a patient's trachea. It should further be noted that the diameter of lower tubular element 24 is less than the diameter of first tubular element 21 and second tubular element 22 so as to facilitate the expelling of gases from said patient's lungs as well as to facilitate the influx of gases to a patient's lungs. It should be further noted that end portion 32 of lower tubular element 24 as depicted in FIG. 2 in the preferred embodiment of the invention forms an internal angle with the axis of lower tubular element 24 of between 30° to 46°, the purpose thereof being to facilitate the passage of lower tubular element 24 past the vocal cords of a patient upon whom anesthetic delivery system 10 is being utilized. Additionally, as further illustrated in FIG. 2, there is formed within the wall of lower tubular element 24, opening 33, opening 33 being a few centimeters from end portion 32 of lower tubular element 24. The purpose of having opening 33 formed through the wall of lower tubular element 24 is to provide a safety feature for anesthetic delivery system 10 such that should the opening of lower tubular element 24 occurring at end portion 32 become obstructed and or blocked due to the accumulation of mucus, and/or other substances, opening 33 provides an alternative pathway for the passage of gases. Nothing herein should be construed as limiting the invention to the fact that end portion 32 defines an angle as illustrated in FIG. 2 of between 30° to 46° as related to the axis of lower tubular element 24, it being within the scope of the invention that end portion 32 could define any angle between 20° and 90°. Additionally, in the preferred embodiment of the invention illustrated in FIG. 2 of the drawings, the distance between the location of the opening 33 in relationship to end portion 32 can vary anywhere from between 0.5 centimeters to 1.0 centimeters although nothing herein should be interpreted to so limit the invention.

The means to selectively inflate and/or deflate inflatable balloon element 23 is by the utilization of delivery tube 25 which is attached at one end to bulb member 26. As depicted in FIG. 2, bulb member 26 is hermetically coupled to delivery tub 25 at one of its ends. Delivery tube 25, as depicted in FIG. 2 and FIG. 3 passes through the wall of second tubular element 22 and extends down through the interior wall of second tubular element 22 to a point where it then is hermetically coupled to an opening in the wall of second tubular element 22, said point being at the portion of lower tubular element 24 wherein inflatable balloon element 23 is positioned.

It should be noted that as a result of this structural arrangement, there is the ability to inject air into bulb member 26 by use of a syringe or other such means in a manner well known in the prior art which in turn then causes inflatable balloon element 23 to inflate uniformly about the exterior of lower tubular element 24, thereby sealing off a patient's trachea. An experienced physician utilizing anesthetic delivery system 10 can determine by the squeezing of bulb member 26 when the appropriate and desired pressure level is reached as related to the inflation of balloon element 23. To deflate inflatable balloon element 23 once same has been inflated in accordance with the above, one merely inserts into bulb member 26 a syringe whose plunger has been compressed. Upon pulling out the plunger, one is able to, in effect, draw air out of the closed system comprising bulb member 26, delivery tube 25 and inflatable bulb element 23 thereby deflating balloon element 23.

The injection of air into bulb member 26 by use of a syringe is also well known in the prior art. A one-way valve member 34 attached to said bulb member 26, as well known within the prior art, accomplishes same. As taught in the prior art, when the syringe is not attached to one-way valve member 34 of bulb member 26, the valve member 34 associated therewith is closed thereby preventing air from either going into or out of bulb member 26. Upon the attaching of a syringe to one-way valve member 34 of bulb member 26, in a manner well known in prior art mechanisms, the one-way valve member 34 of bulb member 26 is opened thereby allowing for either the injection therein of gas from said syringe or the removal of gas therefrom by the syringe. Upon disconnection of the syringe from one-way valve member 34 of bulb member 26, the valve associated therewith is then placed into its closed position. It is well known in the prior art that a device known as "pilot balloon" is a structure equivalent to that addressable to one-way valve member 34 in combination with bulb member 26.

Additionally depicted in FIG. 2 and in keeping with the invention, is sampling tube 27. Sampling tube 27 has one end that is outside of endo-tracheal tube element 20 while the remaining portion of sampling tube 27 passes through, in an airtight fashion, the wall of second tubular element 22 and ends within second tubular element 22 at opening 28. Opening 28 is an opening in the wall structure of second tubular element 22 where first tubular element 21 is hermetically coupled thereto.

The purpose and function of sampling tube 27 is to provide a means for monitoring the levels of the various gaseous components that make up the content of the gas located in second tubular element 22 at the point where opening 28 is formed therein. As a result, a patient can have monitored the composition and/or make up of the gases occurring at said location to determine carbon dioxide levels as well as other pertinent data during an operative procedure wherein anesthetic delivery system 10 is utilized. Although not illustrated in FIG. 2, a structure comparable to one-way valve member 34 can be utilized and otherwise hermetically coupled to the exterior end of sampling tube 27 which, as illustrated in FIG. 2, is exterior to endo-tracheal tube 20 so as to provide a means to selectively remove and otherwise monitor the composition of the gases occurring within anesthetic delivery system 10 at a point adjacent to opening 28 of second tubular element 22. As a result, a patient's carbon dioxide level during a medical procedure wherein anesthetic delivery system 10 is utilized can be constantly monitored.

As further depicted in FIG. 2, that portion of endo-tracheal tube 20 that is within the mouth of a patient when anesthetic delivery system 10 is utilized, is depicted therein by bracket 29. As further depicted in FIG. 2, tubular element 21 opens into second tubular element 22 at opening 28 formed in second tubular element 22.

As additionally illustrated in FIG. 2, lower tubular element 24 is of a diameter that is less than dimension "a" of second tubular element 22 as depicted in FIG. 3 as well as less than dimension "b" of second tubular element 22 as depicted in FIG. 3. By having lower tubular element 24 of a diameter less than the dimensions of "a" and "b" as set forth in FIG. 3, there is facilitated the ability of a patient utilizing anesthetic delivery system 10 to expel gases from said patient's lungs without encountering a build up of pressure and/or resistance adverse to said expelling of gases due to the dimensions addressable by designations "a" and "b" of second tubular element 22 as depicted in FIG. 3 as compared to the diameter of lower tubular element 24.

In keeping with the invention, it should be noted that there is no "dead space" within anesthetic delivery system 10 addressable to coupling element 11, filter element 12, elbow element 13 and the portion of endo-tracheal tube 20 that exists between opening 28 of second tubular element 22 and the point where endo-tracheal tube 20 is coupled to elbow element 13 as illustrated in FIG. 2. The only volume of "dead space" in the design of the system is that attributable with the volume associated with the portion of anesthetic delivery system 10 designated by bracket 30 as illustrated in FIG. 2 which is defined as that portion of endo-tracheal tube 20 between end portion 32 of lower tubular element 24 and the point of opening 28 formed within the wall of second tubular element 22 that is closest to elbow element 13 as illustrated in FIG. 2.

As illustrated in FIG. 2, the volume of "dead space" inherent in anesthetic delivery system 10 and as further addressable by bracket 30 is approximately 5 milliliters in volume in the preferred embodiment as illustrated in FIG. 2 as compared to the overall volume addressable by the preferred embodiment illustrated in FIG. 2 of approximately 150 milliliters. Thus, the dead space inherent in anesthetic delivery system 10 is approximately 3% of its overall volume. Additionally, as illustrated in the preferred embodiment of FIG. 2, endo-tracheal tubular element 20 is approximately 30 centimeters in length and the internal diameter of lower tubular element 24 can range between 2.5 millimeters for a premature infant to 9 millimeters which would be addressable to an adult weighing over 200 pounds. It is within the scope of the invention that the internal diameter of lower tubular element 24 shall vary in accordance with the above parameters, same being within the knowledge and expertise of a physician utilizing anesthetic delivery system 10, depending upon the size of the patient. It should be further noted that in the preferred embodiment illustrated in FIG. 2, the diameter of lower tubular element 24 is approximately 1 millimeter smaller than the dimension designated as "b" of second tubular element 22 as illustrated in FIG. 3. It should be further noted that nothing herein should be considered to limit the invention to such a measurement, it being within the scope of the invention to have the diameter of lower tubular element 24 be of a diameter less than the dimension designated as "b" of second tubular element 22 as illustrated in FIG. 3, independent of a specific numerical amount.

As envisioned with regard to the implementation of the invention, various sizes as addressable to the diameter of lower tubular element 24, second tubular element 22 and first tubular element 21 as depicted in FIG. 3 would be readily available to a physician who seeks to utilize anesthetic delivery system 10, said sizes to vary so as to accommodate a range of patients from that of a premature infant to an adult weighing over 200 pounds.

In keeping with the invention, and as illustrated in FIG. 4, there is illustrated therein extension element 40 which is capable of being inserted between coupling element 11 and filter element 12 so as to provide a means of extending and/or lengthening the pathways whereby gases being injected by way of inner tubular element 15 and gases being expelled through outer tubular element 14 is achieved.

In keeping with the invention, the overall length of extension element 40 can be anywhere from a foot or two in length to lengths as much as ten feet, twenty feet or thirty feet, the only limiting factor being the length necessary to provide the above referenced couplings while a patient is undergoing a medical procedure wherein the patient is of necessity distanced from the initiating source of anesthesia.

As depicted in FIG. 4, extension element 40 comprises outer tubular element 41 and an inner tubular element 42, inner tubular element 42 being concentrically positioned within outer tubular element 41 as the result of spoke members 43.

In further keeping with the invention, outer tubular element 41 is capable of being hermetically selectively coupled to outer tubular element 14 of coupling element 11 as well as to outer tubular element 17 of filter element 12 when same is utilized while inner tubular element 42 is hermetically selectively coupled to inner tubular element 15 of coupling element 11 and inner tubular element 16 of filter element 12.

Although extension element 40 is not utilized nor needed to be utilized in each and every application of anesthetic delivery system 10, extension element 40 is available when the circumstances are warranted.

It should also be noted that the material to be utilized in the fabrication of endo-tracheal tubular element 20, coupling element 11, filter element 12, elbow element 13 and extension element 40, can be any composition of material well known in the prior art that has been utilized in prior art devices addressable to the same function as set forth herein, said material to include but not be limited to rubber, silicone (polysiloxane), polyethylene, polyvinyl chloride (PVC) and/or TEFLON® (polytetraflouroethylenes).

In further keeping with the invention, should anesthetic delivery system 10 be utilized with regard to an infant, inflatable balloon element 23 would be omitted along with one-way valve member 34, bulb member 26, and delivery tube 25 since, under such circumstances, the diameter of lower tubular element 24 utilized in such a circumstance would be sufficient to achieve the sealing of said infant's trachea.

As a result of the inherent design of anesthetic delivery system 10, and in keeping with the invention, the "dead space" evidenced by bracket 30 remains constant, independent of the dimensions of coupling element 11, filtering element 12 and elbow element 13.

Figure 5:
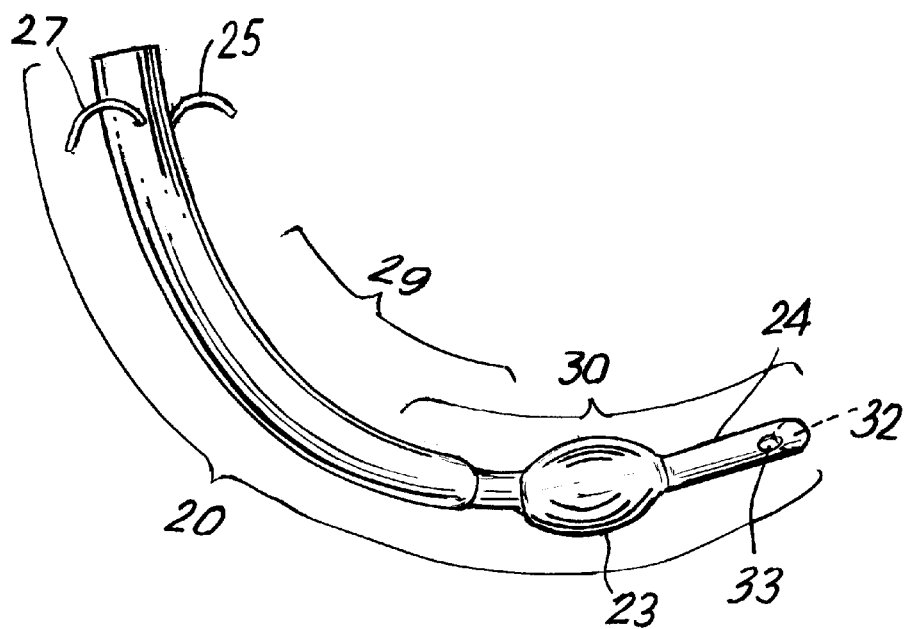
FIG. 5 is a side elevational view of that portion of FIG. 2 designated by numerical reference "20".

In further keeping with the invention, it should also be noted that endo-tracheal tube element 20 in the preferred embodiment depicted in FIG. 5 evidences an arced structure as viewed from the side, which facilitates its insertion through the mouth and into the trachea of a patient.

It will be understood that the foregoing general description and the following detailed description as well are exemplary and explanatory of the invention, but are not restrictive thereof.

The accompanying drawings referred to herein and constituting a part hereof, are illustrative of the invention but not restrictive thereof, and, together with the description, serve to explain the principles of the invention.

I claim:

1. An anesthesia delivery system for minimizing the build up of carbon dioxide levels in a patient due to a patient re-breathing their own exhaled gases, said system compromising:

a) an endo-tracheal tube element capable of being inserted through a patient's mouth, said endo-tracheal tube element comprising;

i) a first hollow tubular element defining a first opening at one end of said first hollow tubular element and a second opening at the other end of said first hollow tubular element, said first opening of said first hollow tubular element being capable of being hermetically coupled to a source of gas that is to be injected in a patient's lungs;

ii) a second hollow tubular element defining a first opening at one end of said second hollow tubular element and a second opening at the other end of said second hollow tubular element, said first opening of said first hollow tubular element of said endo-tracheal tube element being concentrically positioned within the first opening of said second hollow tubular element and wherein said first opening of said second hollow tubular element being capable of being hermetically coupled to an outside source for eliminating expelled gases form said patient and formed so that said second opening of said first hollow tubular element is hermetically coupled to said second hollow tubular element at said second opening of said second hollow tubular element, wherein said first hollow tubular element of said endo-tracheal tube element and said second hollow tubular element of said endo-tracheal element utilize a common wall between their respective structures for a portion of their length, iii) a lower hollow tubular element hermetically coupled to said second hollow tubular element at said second opening of said second hollow tubular element;

b) means hermetically coupled to said first opening of said first hollow tubular element for delivering a source of gas to said first hollow tubular element of said endo-tracheal tube element;

c) means hermetically coupled to said first opening of said second hollow tubular element for eliminating expelled gases from said second hollow tubular element of said endo-tracheal tube element; and d) a filtering element capable of maintaining the moisture level within a patient's pulmonary tree while blocking the expelling of contaminants, said filtering element being hermetically coupled between the endo-tracheal tube element and said means delivering said source of gas and said means for eliminating said expelled gases whereby the introduction into said anesthesia delivery system of said filtering element does not increase the "dead space" of said system.

2. An anesthesia delivery system as described in claim 1 wherein means are provided for withdrawing from said endo-tracheal tube gases appearing at a location therein wherein said second opening of said first hollow tubular element is hermetically coupled to said second hollow tubular element.

3. An anesthesia delivery system as described in claim 1 wherein the diameter of said lower hollow tubular element that is hermetically coupled to said second hollow tubular element is less than the diameter of said second hollow tubular element.

4. An anesthesia delivery system as described in claim 1 wherein said lower hollow tubular element defines an opening at its end opposite to its end that is hermetically coupled to said second hollow tubular element such that a cross-section of said lower hollow tubular element taken parallel to the axis of said lower hollow tubular element defines an opening having an angle of between 30° and 46° with said axis.

5. An anesthesia delivery system as described in claim 1 wherein a selectively inflatable balloon means is coupled about the exterior wall of said lower hollow tubular element so as to selectively seal off the tracheal passageway of a patient upon the inflation of said balloon means such that no gas can pass between the outside wall of said lower hollow tubular element and the patient's trachea.

6. An anesthesia delivery system as described in claim 1 wherein said endo-tracheal tube element defines an arc.

7. An anesthesia delivery system described in claim 1 wherein said filtering element comprises:
   a) an outer tubular element;
   b) an inner tubular element structurally positioned within said outer tubular element such that gases passing through said inner tubular element do not come in contact with gases passing through said outer tubular element; and
   c) means for positioning within said outer tubular element filtering material capable of maintaining the moisture level within a patient's pulmonary tree while blocking the expelling of contaminants.

8. An anesthesia delivery system as described in claim 1 additionally comprising an extension element comprising an inner hollow tubular element and an outer hollow tubular element, said inner hollow tubular element being concentrically structurally positioned within said outer hollow tubular element, said inner hollow tubular element and said outer hollow tubular element being of identical lengths and defining a first opening for each hollow element and a second opening for each hollow element at their respective ends, said extension element being capable of being hermetically coupled between said endo-tracheal tube element and said means delivering said source of gas and said means for eliminating said expended gases whereby the introduction into said anesthesia delivery system of said extension element does not increase the "dead space" of said system.

* * * * *